United States Patent [19]
Varani

[11] 3,933,628
[45] Jan. 20, 1976

[54] METHOD AND APPARATUS FOR THE ANAEROBIC DIGESTION OF DECOMPOSABLE ORGANIC MATERIALS

[75] Inventor: Frederick T. Varani, Golden, Colo.
[73] Assignee: Bio-Gas of Colorado, Inc., Denver, Colo.
[22] Filed: July 10, 1974
[21] Appl. No.: 487,039

[52] U.S. Cl. .................. 210/12; 126/271; 210/170; 210/187
[51] Int. Cl.² ........................ C02C 1/14; F24J 3/02
[58] Field of Search ......... 61/.5, 1 R; 126/270, 271; 195/1; 210/2, 11, 12, 16, 170, 180, 187

[56] References Cited
UNITED STATES PATENTS

| | | | |
|---|---|---|---|
| 3,077,190 | 2/1963 | Allen | 126/271 |
| 3,125,091 | 3/1964 | Sleeper, Jr. | 126/271 |
| 3,246,761 | 4/1966 | Bryan et al. | 210/12 X |
| 3,330,118 | 7/1967 | Biais | 126/270 X |
| 3,383,309 | 5/1968 | Chandler | 210/11 |
| 3,390,672 | 7/1968 | Snelling | 126/271 |
| 3,493,494 | 2/1970 | Knibb | 210/12 X |
| 3,537,267 | 11/1970 | Webb | 61/1 R X |
| 3,620,206 | 11/1971 | Harris, Jr. et al. | 126/271 |
| 3,707,850 | 1/1973 | Connell et al. | 61/.5 X |
| 3,736,754 | 6/1973 | Azalbert et al. | 61/.5 |
| 3,768,264 | 10/1973 | Best | 126/271 X |
| 3,838,199 | 9/1974 | Coe et al. | 210/2 X |

OTHER PUBLICATIONS

D. E. Bloodgood, Gas from Sewage Sludge, Nov. 1954, Water & Sewage Works, pp. 512–514.

*Primary Examiner*—Charles N. Hart
*Assistant Examiner*—Robert H. Spitzer
*Attorney, Agent, or Firm*—Edwin L. Spangler, Jr.

[57] ABSTRACT

This invention relates to an improved anaerobic digestion apparatus for decomposable organic materials characterized by a digestor covered and sealed by a liquid-filled pond heated with solar energy. The effluent from the fermentation reaction taking place in the digestor has excellent absorptivity for solar energy and is advantageously used as the heat transfer medium filling the pond. The pond is covered with a translucent roof capable of transmitting solar energy, such roof cooperating with the liquid-filled pond therebeneath to produce an artificial environment of reduced sensitivity to atmospheric conditions which is operative to help maintain a condition of stable equilibrium within the digestor. In the preferred embodiment, the vessel forming part of the digestor in which the fermentation reaction takes place comprises an excavated trench lined with a suitable fluid-impermeable membrance while the roof over the pond consists of an inflatable air-supported bubble. Also preferred is to float the pond upon the fermenting material in the digestor by covering the latter with a flexible fluid-filled float-supported membrane. The invention also encompasses the novel method of carrying out anaerobic digestion of decomposable organic materials which includes sealing and insulating the open-topped reaction vessel by covering same with a fluid-filled pond, heating the fluid in the pond with solar energy, and circulating the fluid thus heated through the feedstock in the digestor so as to maintain a near constant temperature therein conducive to fermentation. The invention further includes such novel steps as floating the pond upon the fermenting feedstock in the digestor, burying the reaction vessel to minimize heat transfer through the walls thereof, and establishing a self-regulating environment above the digestor which insulates same from the more radical, and sometimes extreme, fluctuations in atmospheric temperature and light conditions occurring outside thereof.

11 Claims, 6 Drawing Figures

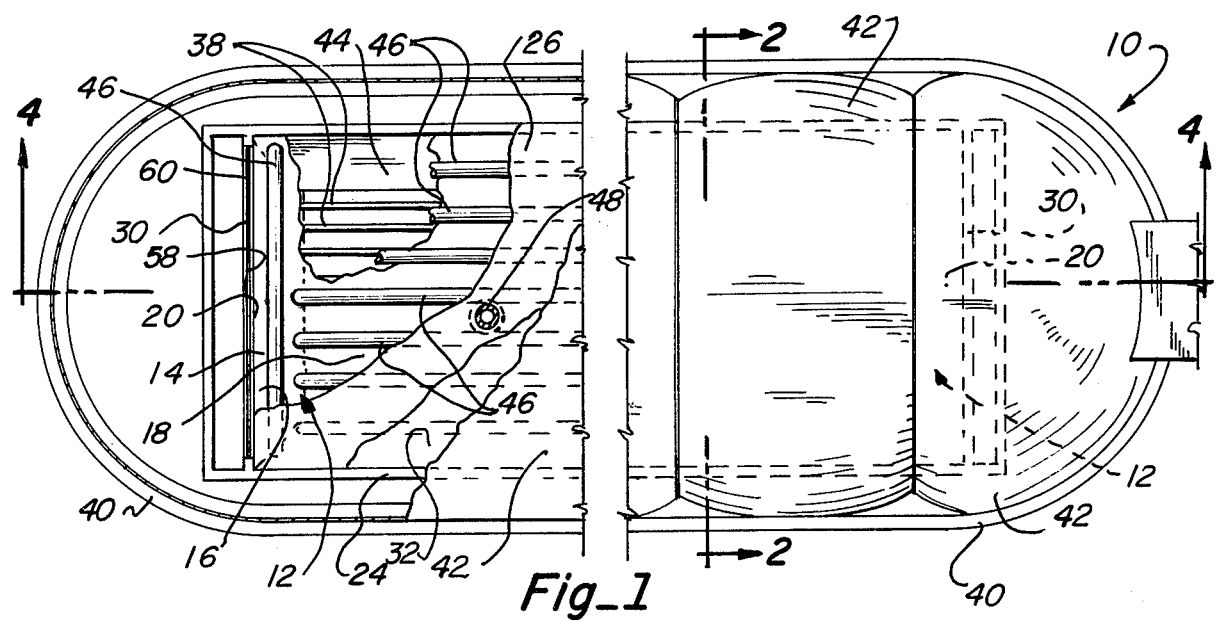
Fig_1
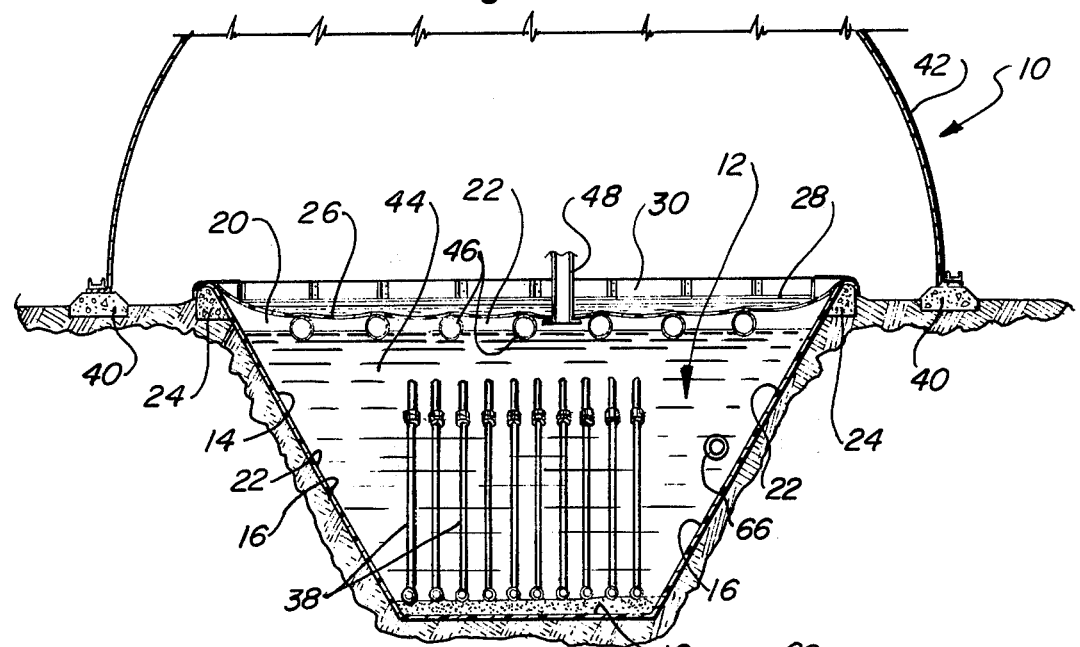
Fig_2
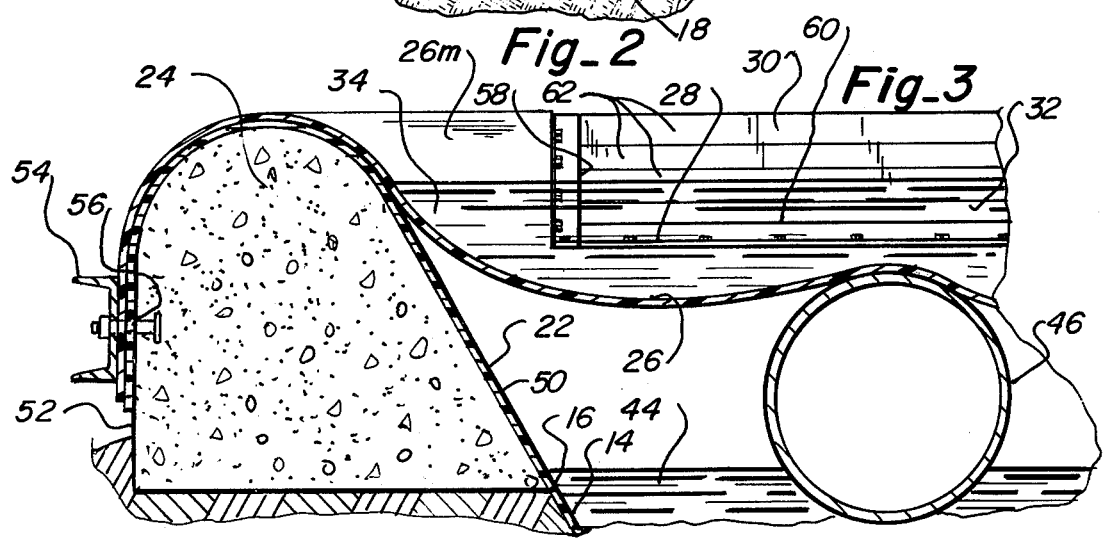
Fig_3

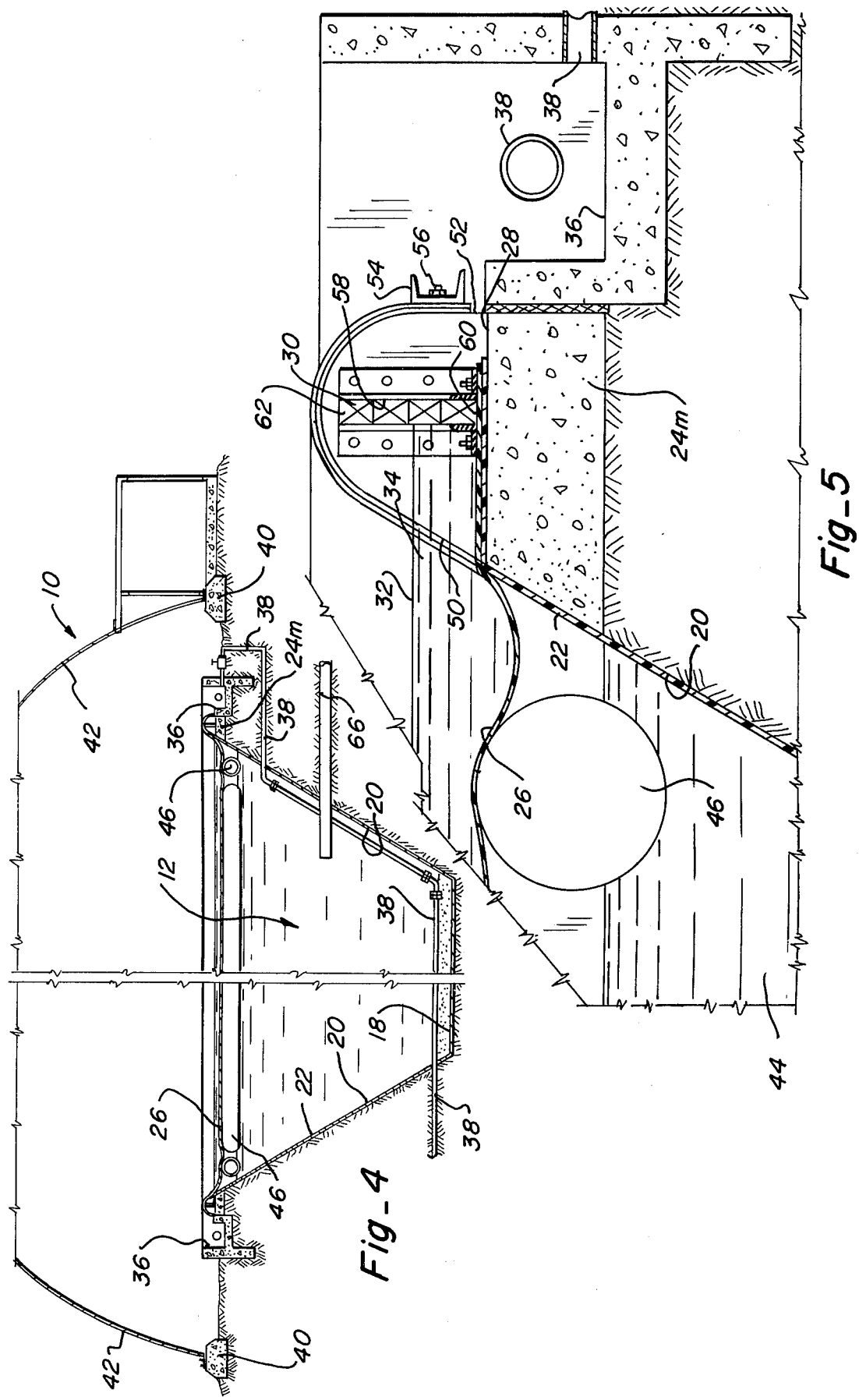

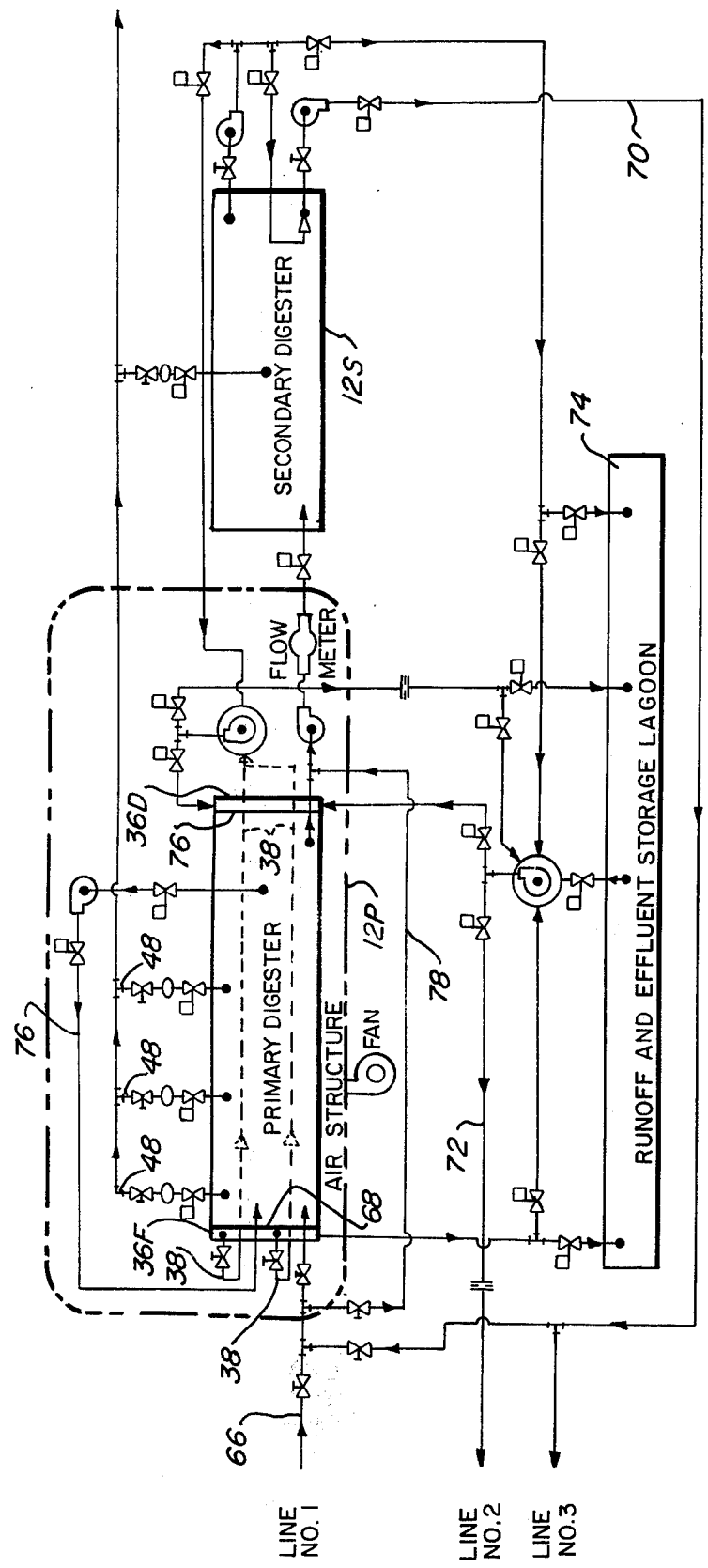
Fig_6

METHOD AND APPARATUS FOR THE ANAEROBIC DIGESTION OF DECOMPOSABLE ORGANIC MATERIALS

Anaerobic digestion systems for decomposable organic waste materials are widely known and used, especially in the production of clear, potable water in a waste water treatment facility. All such systems result in the production of so-called "bio-gas" resulting from the action of the methanogenic bacteria on the organic feed material. This bio-gas by-product is a mixture of methane, carbon dioxide and hydrogen sulfide. More specifically, bio-gas is about 70% methane, 30% $CO_2$ and a trace, 10ppm or so, $H_2S$. Once the $CO_2$ and $H_2S$ are removed or at least reduced to acceptable limits, the methane is usable and marketable just the same way as natural gas.

The bio-gas generated in a waste water treatment facility is either consumed or flared as waste gas and it is always considered as a by-product, the primary product being the clean water. Nevertheless, the principles and techniques used in waste water treatment can, with certain changes, be made adaptable to a synthetic fuels facility where the emphasis becomes one of gas production rather than potable water. These changes amount to a modification of the feed composition so as to optimize gas production, selecting operating temperatures most favorable to the methane-producing (methanogenic) bacteria and controlling the latter through the use of a novel solar-heated heat sink covering the digestor so as to prevent "temperature-shock" in the bacteria.

Now, while the potential of tremendous volumes of organic waste materials as a source of fuel has long been recognized, to date none has succeeded in building a processing plant that is practical from a commercial standpoint due to the unfavorable economics and the particular technical problems involved. Some of these problems are general in nature in that they effect the practicality of any anaerobic digestion system regardless of what type of decomposable organic waste material is used as a feed, a few of the more important of which are as follows:

1. Huge sealed tanks are needed which possess the capacity to handle the tremendous volume of feedstock that must be processed in order to realize any commercially significant output of gas.
2. The feedstock must be mixed, specially prepared and, perhaps, even treated before being introduced into the digestor so that it can be handled efficiently, will enter and remain compatible with the bacteria, and is optimized from a chemical standpoint for gas production.
3. Once in the digestor, the feedstock has to be mixed to promote efficient bacterial action and the temperature of the system must be controlled and maintained within a degree or two one way or the other at levels in excess of 90°F.

While there are many known sources of decomposable organic waste materials susceptible of undergoing anaerobic digestion and producing bio-gas as a result thereof, probably one of the most significant ones is manure. Manure, in addition to the ever-present problem of its odor, creates a number of special problems which, in some instances at least, contribute to the already overwhelming problems associated with using anaerobic digestion of decomposable organic wastes as the means for generating methane. One very serious problem is that in gathering up the manure to be processed, it is never free of dirt, sand, straw and other contaminants present in the area where the cattle are confined and much of which may have to be removed prior to its being treated. Barnyard manure from cattle allowed to forage for themselves as opposed to feedlot manure is, in addition, inconsistent in texture and other physical characteristics which makes it difficult to handle and poses a multitude of sizing, pumping and piping problems. Furthermore, barnyard manure often differs chemically from feedlot manure in that it usually contains a considerably higher proportion of constituents which are not effected by bacterial action and, as a result, eventually form a scum on the surface of the digestor which has to be removed.

It has now been found in accordance with the teaching of the instant invention that these and other shortcomings of the prior art facilities and methods for the anaerobic bacterial decomposition of organic waste materials can, in large measure, be overcome by the simple, yet unobvious, expedient of covering and sealing the digestor with a liquid-filled pond forming a heat sink, then roofing over the latter with a translucent dome, preferably inflatable, which transmits solar energy to the fluid in the sink, and then using the fluid thus warmed as the heat transfer medium for maintaining the digestor temperature within prescribed limits. The digestor preferably comprises a trench capable of retaining the feedstock, the open top of which is both closed and sealed by means of a cover that functions as the receptacle for the fluid in the pond atop thereof. This cover can float on the feedstock slurry in the digestor and the effluent from the digestor is ideally suited for use as the heat transfer medium in the pond because its dark brown to black color is highly absorptive of the solar energy. By using an inflatable bubble as the translucent dome or canopy over the digestor in place of a rigid structure, considerable cost savings are effected, especially in large scale installations.

It is, therefore, the principal object of the present invention to provide a novel anaerobic digestion system.

A second objective of the invention is to provide a system of the type aforementioned wherein solar energy is used to heat same.

Another object of the within-described invention is to provide a unique method of carrying out the anaerobic digestion of decomposable organic waste materials with special emphasis upon the storage and conservation of solar energy in a heat transfer medium used to maintain an essentially constant temperature environment.

Still another objective of the invention herein disclosed and claimed is to utilize the effluent from the digestor along with cover sealing same as the means for confining the bio-gas, generated in the latter, the heat transfer media within which the solar energy is stored and, lastly, as the insulation that prevents the feedstock from overheating or becoming too cool as the ambient temperature inside the translucent dome fluctuates.

An additional objective is to use the dome-covered pond as the means for creating an artificial environment that helps maintain a near constant temperature in the digestor despite wide variations in outside temperature, atmospheric conditions and daylight.

Other objects will be in part apparent and in part pointed out specifically hereinafter in connection with the description of the drawings that follows, and in which:

FIG. 1 is a fragmentary top plan view of the primary digestor, portions of which have been broken away to reveal it covered by a floating pond and the pond, in turn, covered by an inflatable translucent bubble;

FIG. 2 is a section taken along line 2—2 of FIG. 1 to a greatly enlarged scale;

FIG. 3 is a fragmentary section still further enlarged showing the details of the trench bank, the liner for the trench, the floating pond liner and the end wall structure;

FIG. 4 is a longitudinal section taken along line 4—4 of FIG. 1 and to the same scale as FIG. 2, portions of the center section having been broken away and deleted to conserve space;

FIG. 5 is an enlarged fragmentary section similar to FIG. 3 and to the same scale as the latter showing the details of the wiers at opposite ends of the trench; and, FIG. 6 is a schematic flow diagram showing the primary and secondary digestions, effluent lagoon and associated fluid-transfer piping employed in the fermentation of bio-degradable feedlot wastes that form part of a plant whose primary objective is the production of methane and carbon dioxide.

Before referring specifcally to the drawings, it will be helpful to mention that the invention forming the subject matter hereof will be described in connection with a large scale plant for the anaerobic digestion of commercial feedlot waste with the primary objective of such a plant being the production of methane for use as a gaseous fuel. It is in such a plant as this that the economics inherent in the design make the production of gaseous fuel commercially practicable; yet, this same system with but minor modification of a type well within the skill of an ordinary artisan, will function equally well for waste water treatment or, for that matter, the anaerobic digestion of any biodegradable organic waste. In fact, if the end product of the process is other than a low-priced fuel such as, for example, hydroponically-grown flowers, vegetables and the like, than a smaller installation becomes commercially attractive where one could conceivably afford a rigid translucent solar dome in place of an inflatable one and replace the trench-type digestor dug into the ground with a more conventional reaction vessel. Be that as it may, regardless of the particular end product produced by the system, its novel features remain germane thereto.

Since the instant anaerobic digestion system has been illustrated and will be described in connection with a plant to produce methane through the bacterial degradation of feedlot wastes, it would be well to first examine the conditions, both favorable and unfavorable, under which such a plant must operate. To begin with, the magnitude of such an operation becomes somewhat difficult to comprehend in that a large feedlot will have a "standing population" of around 100,000 cattle at any one time. These cattle are introduced into the pens at an average weight of around 700 pounds each and sold, after being fed for five months, at an average weight of 1100 pounds.

The cattle are confined in pens to maximize their food intake while allowing only minimal exercise thus bringing about the greatest weight gain during the period of confinement. Fortunately, in order to achieve the maximum possible weight gain, the feed is specially formulated and its consistency results in the manure being consistent also. Moreover, the digestive system of a bovine animal utilizes bacteria similar to that employed in the digestor of the instant sytem, therefore, the specially formulated feed results in a manure which, likewise, is both physically and biologically ideally suited to the anaerobic process utilized in the method and apparatus forming the subject matter hereof.

After the cattle are "fed-out", the pens are emptied and the manure is scraped therefrom and removed for processing along with a substantial amount of soil, debris and other contaminants. Despite these contaminants, the manure is remarkably uniform even to its physical characteristics which make it easy to process mechanically into a mixture that can be processed easily and efficiently. The startling fact is that a 100,000 cow feedlot will generate a mixture each day of slightly over 3.3 million pounds of manure and dirt to be processed. This is only part of the story in that almost 6 million pounds of water is added to this waste material each day along with nearly 200,000 pounds of carbon, bringing the total weight of the feedstock being introduced into the system during each 24 hour period in excess of 9 million pounds on an average.

Now, a conventional facility capable of processing this magnitude of material on a daily basis would, in addition to being huge, be so costly as to become uneconomical especially when used as a plant to produce primarily methane. For instance, the primary and secondary digestors must each have a volume or capacity of upwards of 1⅔ million cubic feet which translates into two tanks some 40 feet deep, 82 feet wide and 700 feet long. An ordinary above-ground structure of this size would be very expensive to say the least; therefore, in accordance with the teaching of the instant invention a novel and inexpensive substitute therefore will be used which has been illustrated in FIGS. 1 through 5 of the drawings to which detailed reference will now be made.

The anaerobic digestion apparatus has been designated broadly by reference numeral 10 and it will be seen to include a digestor similarly designated by numeral 12 which, in the particular form shown, comprises an excavated trench 14, the sides 16, bottom 18 and ends 20 of which are overlayed and sealed with a fluid impervious liner 22. A poured concrete rein 24 borders the entire trench and provides the footing to which the liner 22 and the cover 26 are anchored. In the particular form shown, the portions 26m of the rim 26 located at the ends of the trench (FIGS. 4 and 5) are truncated to produce horizontally-disposed platforms 28 atop which are erected variable height wiers 30 over which the liquid heat transfer medium 32 is allowed to flow from pond 34 atop cover 26 preparatory to being circulated through the feedstock sludge where it is used to maintain the latter at an essentially constant temperature. Bordering the truncated end sections 24m of the rim on the outside thereof are a pair of open-topped concrete tanks 36 positioned at opposite ends that receive the heat transfer medium 32 which has overflowed the wiers. The effluent in these tanks will be pumped therefrom through an underground piping system 38, the function of which is to circulate the heat transfer medium through the sludge in the digestor.

Bordering the trench 14 on the outside of the rim are concrete footings 40 to which the inflatable translucent dome or canopy 42 is anchored to provide a roof over the digestor 12. The heat transfer medium 32 in the "floating" pond 34 is, of course, heated by the sun during the daytime while at night the moisture present inside the dome condenses on the cold surface thereof giving up heat in the process which helps to maintain an essentially constant temperature environment. The cover 26 is supported atop the feedstock slurry 44 in the trench upon floats 46. This cover 26 is sealed to the trench liner 14 along the rim of the trench and cooperates therewith to define the anaerobic digestor 12 broken only by the vent 48 (FIG. 2) through which the bio-gas is withdrawn for further processing.

At this point it might be wise to explore in somewhat greater detail the various elements of the digestion system 10 for which purpose specific reference will be made to FIGS. 2–5, inclusive. First of all, the trench 14 is shown excavated to provide downwardly and inwardly sloping side and end walls thus producing a large trough with trapazoidal cross sections both longitudinally and transversely. As already noted, a plant to handle the manure from a 100,000 cow feedlot will require two such trenches with each being 700 feet × 82 feet × 40 feet deep and having a capacity of 12.5 million gallons.

The poured concrete rim 24 bordering each tank has, as its prime purpose, the anchoring of both the trench liner 22 and the floating cover 26. In the particular configuration shown, it is round on top and has an inside wall 50 (FIG. 3) inclined at the same angle as the trench wall so as to form a coplanar continuation of the latter. The cover and trench liner are both draped across the rounded top edge and down along the outside wall 52 to which they are secured by a length of channel iron 54 bolted onto studs 56 projecting from the rim in which the heads are buried. Those truncated rim sections 24m at the ends of the trench merely have the cover and liner draped across horizontal surface 28 at which point they are anchored down by the wier 30 fastened atop the latter as shown in FIG. 5.

Rubber lined excavations are not novel but they do provide the necessary capacity at a cost for below that of surface tanks regardless of how they are made. For instance, rubber lined excavations are figured at current prices at around $0.02/gallon including excavation costs, whereas, conventional surface tanks cost anywhere from 2½ to 5 times this much. It is presently purposed to line the trenches with a reinforced rubber-like material having a thickness in the neighborhood of 30 mils. While the same rubberized material may be used for the trench cover 26, it will carry a considerable hydrostatic load at least in the primary digestor and, for this reason, will have to be made from heavier stock say, for example, 45 mill material.

The floats 46 are cylinders of polystyrene that are buoyed up by the feedstock sludge 44 filling the trench. The rubber cover 26 is draped from float to float as shown in FIGS. 2 and 3 where it functions in cooperation with the trench liner to seal the interior of the digestor from the atmosphere and thus permit it to operate anaerobically. As will appear presently, the second stage digestor really can function quite well without the pond 34 overlying same; therefore, the floats 46 can, if desired, be eliminated altogether because the pressure of the bio-gas generated beneath the cover is entirely adequate to support same. The placement of the floats is, of course, a matter of choice just so long as enough of them are being used to adequately support the liquid-filled cover.

Pond 34 overlying the digestor is, in all probability, the most important single feature of the invention. At least the primary digestor has this pond filled with fluid to a depth of between 2 and 6 inches at all times. The effluent from the digestor itself is ideally suited for use as the heat transfer medium 32 that fills the pond 34 because it is dark brown to black in color and provides excellent heat absorptivity. It flows from pond 34 over the wiers 30 into the open-topped tanks 36 located at opposite ends of the digestor. It can then be pumped from these tanks and circulated through the heat exchanger 38 laid in the bottom of the trench.

These wiers are best revealed in FIGS. 3 and 5 and they will be seen to comprise nothing more than upright channels 58 and a transverse channel 60 defined between the spaced parallel flanges of back-to-back angle irons fastened to the horizontal surface 28 atop truncated rim 24m and the vertically-extending walls at the ends thereof. A series of 2 × 4 boards 62 are stacked one atop the other with the ends thereof confined within the upright channels as shown. The effective height of the wiers can, of course, be altered by removing one or more boards from the stack thereof and permitting the effluent to overflow those that are left into the holding tanks. The depth of the effluent in the pond is a function of how much is allowed to overflow the wiers into the holding tanks although, to some extent at least, its maximum depth is controlled by how full the trench is filled with the feedstock sludge. By carefully controlling the temperature of the effluent heat transfer medium in a manner to be set forth in detail presently, the temperature within the digestor can be maintained at a near constant level.

The only opening in the cover 26 admits vent 48 through which the bio-gas is withdrawn from the digestor for further processing to remove the $CO_2$ and $H_2S$. Vent 48 is not, of course, open to the atmosphere, but rather, comprises a part of a closed system terminating in a gas storage facility.

The canopy 42 covering the digestor 12 comprises an important as well as an integral part of the digestion system as it not only transmits the solar energy to the heat transfer medium 32 in the pond 34 but, in addition, cooperates therewith to produce an artificial environment which is conducive to the conservation of the heat necessary to maintain the digestor at a constant temperature. While, as previously noted, a rigid translucent dome-like structure will function just as well in the instant anaerobic digestion system, its cost would be prohibitive in the size required to cover the digestors, especially in a fuel gas production facility; therefore, an inflatable plastic bubble constitutes the only practical solution. The material for such a bubble must transmit as much of the spectral and diffuse solar radiation as possible consistent with its possessing the requisite structural strength to withstand expected snow and wind loads, etc. Several such materials are commercially available and are presently used for this same general type of inflatable roof structure. It should be noted in passing that, while the bubble has been characterized herein as being "translucent" in that it must transmit solar energy to the heat transfer medium, it is to be understood that a transparent or semi-transparent roof-forming structure can also be used.

Next, reference will be made to the flow diagram of FIG. 6 for a detailed description of the method of using the previously-described apparatus for the anaerobic digestion of decomposable organic waste materials at a near-constant temperature. While the method is applicable to anaerobic digestion plants processing organic wastes for other purposes than methane recovery as well as those in which the feedstock is other than manure, a plant processing solid feedlot waste to produce fuel as its primary product has been selected for purposes of illustration because the economics made possible in accordance with the teaching of the instant invention are most necessary in such an application.

The raw feedstock enters the primary digestor 12P through feed line 66 where it is deposited at the head end 68 of the latter. This raw feedstock will, upon introduction into the primary digestor, have already been subjected to certain pre-fermentation steps which will vary greatly with the type, condition and end use to be made thereof. For instance, solid feedlot waste materials must first be mechanically sized by means of a screen (not shown) or other apparatus of a similar nature capable of separating the large masses therefrom while passing only those of a given size or smaller. This is followed by a combined gravity separation and dilution step wherein the feedstock is mixed with make-up fluids into a pumpable slurry while, at the same time, the rocks, trash and other heavy solid contaminants are being separated therefrom. This feedstock includes not only the manure to be processed but, in addition, water together with recycled effluent and sludge from the digestion process. If, as in the present example, the plant has as its primary objective the production of gaseous fuel, then additional carbon must be added to the make-up stream, in order to attain a proper chemical (carbon/nitrogen) balance in the feed solids. In addition to carbon itself, the necessary carbon can be added in the form of sawdust, straw or other carbon-rich organic waste. Various types of conventional mechanical mixers and mills can be used to blend the feedstock and reduce its size to a pumpable slurry, none of which has been illustrated here as it forms no part of the present invention.

In addition to the carbon added to the feedstock in proportions such as to provide a carbon/nitrogen ratio of around 25–30 to 1, recycled sludge from the second stage digestor 12S is withdrawn therefrom through sludge line 70 where it is combined with the other components of the feedstock entering the primary or first stage digestor 12P through line 66. This sludge is heavily laden with bacteria and it is used to "seed" the feedstock so that it will commence fermentation immediately upon its being introduced into the digestor.

One additional pretreatment step is necessary in those plants processing feedlot wastes before they can be fed into the digestor, namely, the removal of inorganic solid wastes, particularly, sand and gravel. After each lot of cattle is "fed-out" the pens that housed same are scraped clean and then resurfaced with a sand-gravel mixture, most of which is subsequently removed along with the manure. Since these inorganic wastes are inert insofar as being subject to bacterial attack, they must be removed prior to entering the digestor as the cost of moving them through the system for no useful purpose would be prohibitive. Actually, these substances have an average specific gravity well above that of the active ingredients in the feedstock and, for this reason, they would soon settle out in the digestor and eventually fill it up. Accordingly, in a plant to process feedlot wastes, a classification step is necessary to remove the heavier inorganic solids preparatory to introduction of the decomposable organic wastes into the system. Such a classification is not a difficult one and many standard centrifugal separators and the like will do the job quite adequately and at minimal cost. It should, perhaps, be mentioned that these inorganics carry away with them significant percentages of decomposable organics unless the latter are washed therefrom; accordingly, it is good engineering plant design practice to wash these inorganics prior to disposing of them with the organic-rich effluent from the digestors that is used as part of the make-up fluids in the feedstock. In the schematic, effluent line 72 is used for this purpose and, as shown, it can take effluent from either digestor or effluent storage lagoon 74.

Following completion of the pretreatment steps, the feedstock entering the primary digestor will be relatively free of inert inorganic solids, have a solid particle size in the slurry of around 1/16 inch or smaller, and contain somewhere around 15–18% solids. Additionally, it will have been heavily "seeded" with bacteria by mixing into it active sludge from the second stage digestor. Finally, it will have been chemically tailored to maximize the recovery in accordance with the selected end use. In the case of methane production as previously noted, the feedstock will be chemically adjusted to increase its carbon/nitrogen ratio.

The instant plant contemplates a two-stage digestion process wherein two digestors, a primary one 12P and a secondary one 12S, are connected in series. Both digestors have tanks of the same size in the particular plant illustrated, each having a capacity of about 1⅔ million cubic feet. A feedlot having 100,000 cattle "standing" at one time will, as already noted, produce 3⅓ million pounds of manure per day containing well over 800,000 pounds/day of volatile solids. By the time the pretreatment steps are finished and the feedstock is ready to enter the primary digestor, two of them each having capacities of 12½ million gallons are needed.

These digestors operate on the so-called "plug-flow" reactor principle, namely, the feedstock enters one end of the tank and proceeds slowly through it finally exiting at the discharge end 76. During its journey through the digestor, it passes through a zone of maximum reaction (fermentation) wherein the bacterial action produces the biogas which makes the portion of the slurry thus decomposed relatively lighter than the unreacted portion. As this occurs, vertical motion within the digestor takes place along with the horizontal reaction occasioned by its progress toward the discharge end of the tank. This "self-mixing" as a result of gas evolution contributes to the fermentation reaction as it continually brings the bacteria into contact with fresh (undecomposed) material.

The bio-gas evolved in the fermentation is bled off through the pond covering and sealing the digestor for further processing as represented by gas line 48. This gas has about 10 ppm $H_2S$, 30% $CO_2$ by volume and the rest methane. It, of course, must first be cleaned to remove the particulate matter, then dried to take out the water before being processed to take out the $H_2S$ and $CO_2$. A conventional scrubber can be used to reduce the $H_2S$ concentration to acceptable limits of, say, 1 ppm. Further processing to strip the $CO_2$ therefrom in, for example, an amine-contactor process where the $CO_2$ is absorbed in an aqueous solution of monoethanolamine before being steam stripped leaves essentially pure methane ready for sale.

Now, one of the main prerequisites of an anaerobic digestion system is that of protecting the bacteria against a so-called "temperature shock". These organisms are so sensitive to temperature that they suffer such shocks when the temperature varies as little as a few degrees one way or the other. While the bacterial colony may not actually die as a result of temperature shock, its activity is reduced to an extent that the fermentation reaction stops for all practical purposes; therefore, changes in temperature must be carefully guarded against. Certainly one of the most, if not the most, significant feature of the instant anaerobic digestion method is the way in which the temperature of the system is maintained at a near constant level through the storage of solar energy in fluid heat transfer medium used to both seal and insulate the tank filled with the fermenting decomposable organic waste materials.

The fermentation reaction will proceed satisfactorily at any temperature between approximately 90°F and 115°F, however, between these limits many different species of bacteria become active, each in its own particular temperature zone carved out of this broader range. In other words, the digestion process is basically an equilibrium between many species of bacteria that live upon various substrates (food) and on one another. Changes in temperature cause this equilibrium to shift and some of the more temperature-sensitive species die off or become less active while others assume a more active role.

If, as is being assumed here, the prime purpose of the system is gas production, then so-called "methanogenic" bacteria are responsible and the equilibrium should be shifted to conditions favoring their maximum activity. Unfortunately, methanogenic bacteria are the more sensitive of the species present and, therefore, more susceptible to temperature shock. Ideally, methanogenic bacteria should be kept at about 95°F and the temperature range should not be allowed to vary more than ±2.0°F per day from this base temperature if temperature shock is to be avoided.

The solar energy transmitted through the translucent bubble covering the primary digestor 12P during the daylight hours is, of course, stored in the fluid heat transfer medium 32 filling the pond 34 and, to a lesser extent, by the digestor cover 26 itself. Tremendous amounts of heat can be absorbed and stored in this fashion. For instance, the absorptivity of the fluid heat transfer medium 32 in the pond is 85% or more when the pond is filled with effluent from the digestors. The basic temperature control is maintained within the primary digestor 12P by circulating the heat transfer medium 32 through the feedstock slurry 44 by means of heat exchangers 38 (FIGS. 2, 4 and 6) laid in the bottom of the trench. In the particular form shown in FIG. 6, the heat exchange medium 32 is pumped from the tank 36F at the intake end of the primary digestor 12P, circulated through the heat exchanger 38 laid in the bottom of the latter and then returned to the tank 36D at the discharge end.

During the daylight hours, solar energy is transmitted by the translucent dome and absorbed by the liquid heat transfer medium which evaporates thus preventing the cavity beneath the dome from getting too hot. Conversely, at night, the evaporated water will condense into rain thereby giving up heat to the solar cavity and preventing same from getting too cold. A thermal analysis of the system shows that a tremendous quantity of heat energy can be captured in the above manner, especially when the effluent having an absorptivity at least equal to that of muddy water is used as the heat transfer medium. In fact, depending upon the location of the plant and the available sunlight, too much thermal energy is likely to be a problem rather than too little. Thus, instead of having to supplement the solar energy to maintain the preselected temperature in the digestor, the more probable need is that of a cooling pond represented by storage lagoon 74 in FIG. 6. This lagoon is used to store the effluent during periods of maximum solar energy flux or until needed for heating the digestor such as at night, during prolonged cloudy periods and in extremely cold weather. Once the thermal energy is available in the heat transfer medium, there is, of course, no problem in maintaining the required digestor temperature as these techniques are well known to those experienced in the heating and refrigeration art and, for this reason, they form no part of the instant invention.

One further important step in the process should be mentioned before leaving the subject of the thermal aspects of the system and that is the need for preheating the feedstock prior to introducing same into the intake end of the primary digestor. Obviously, the very "temperature shock" one wishes to avoid would occur if the feedstock entering the digestor was at a temperature other than that of the material already undergoing fermentation therein; therefore, the mix must be preheated to the pre-selected digestor temperature in advance of its entering the latter. Several sources of compatible liquids, both cold and hot are readily available for this purpose. The effluent is, of course, the best source of warm fluid or, alternatively, cooling water from the gas compression facility (not shown). Cooling water will probably be provided by a well or some sort of a cooling lagoon. Some of the heat required to preheat the feedstock is advantageously introduced by recycling part of the semidigested sludge removed from a point near the discharge end of the primary digestor back into the intake end thereof for which purpose the recycled sludge recycle system 76 is employed. The recycled sludge is not only at the correct temperature already but, in addition, the bacteria present therein tend to "reseed" the culture located near the intake end of the digestor thus maintaining the homogeneity thereof and further optimizing gas production.

The process as delineated in FIG. 6 is intended to carry out approximately 80% of the gas production in the primary digestor 12P and the remaining 20% in the secondary digestor 12S. This secondary digestor, while essentially the same size as the primary one due to the fact that it must handle the entire output of the latter is in certain other respects quite different. To begin with, it is quiescent in that no mixing takes place therein and it is unheated. Actually, it comprises an anaerobic settling vessel in which the fermentation reaction commenced in the primary digestor goes to completion. As such, the trench 14 must be lined as at 16 just the same as the primary digestor and it must also be covered and sealed by a cover 26. This cover will not be filled with a heat transfer medium unless, perhaps, additional heat storage capacity is needed for the primary digestor or other parts of the plant. The secondary digestor is, however, preferably covered by inflatable bubble 42 as was the primary one.

Incidental, but nonetheless important, features of the plant are such things as a by-pass line 78 by means of which the feedstock can be admitted directly to the secondary digestor when, for some reason, the first one needs to be shut down for cleaning and the like. Sludge passes from the primary digestor to the secondary one through sludge line 80. Also, sludge line 70 previously mentioned which is used to seed the feedstock with bacteria from the second stage digestor can also be used to introduce well buffered material at a pH of 7.5 or higher from the second stage should a situation occur in which the primary digestor goes "sour" and its pH drops down to 7.0 and below.

A plant such as that outlined above is capable of producing about 8⅓ million ft.$^3$ of bio-gas/day in the first stage digestor and another 1⅔ million ft.$^3$ in the secondary one making a total of nearly 10 million ft.$^3$/day. Of this, one can realize over seven million ft.$^3$/day of methane having a heating value of about 277 million BTU/hour. As by-products of such a facility, the sludge with minimal additional processing can be expected to yield considerable fertilizer. The bio-gas, on the other hand, in addition to methane, will yield 2½ million ft.$^3$ or so of dry $CO_2$/day.

What is claimed is:

1. An anaerobic digestion system which comprises: an open-topped reaction vessel having biodegradable organic reactants therein; a liquid and gas impervious lid sealing the reactants therein; a liquid heat exchange medium covering the lid and cooperating therewith to define a pond; means insulating said pond from the reactants so as to minimize the direct exchange of heat therebetween; translucent roof-forming means covering said pond effective to transmit solar energy to the heat exchange medium contained therein; means associated with said bond for withdrawing the heat exchange medium therefrom and adjusting the temperature thereof to a predetermined level; and, heat transfer means connected to take the heat exchange medium with its temperature thus adjusted and circulate same in heat exchange relation through the reactants to maintain the temperature thereof at a relatively constant level effective to promote fermentation.

2. The anaerobic digestion system as set forth in claim 1 which includes: gas removal means connected into the interior of the reaction vessel for withdrawing gaseous reaction products therefrom.

3. The anaerobic digestion system as set forth in claim 1 in which: the roof-forming means comprises an inflatable air-supported structure.

4. The anaerobic digestion system as set forth in claim 1 in which: the means insulating said pond from the reactants comprises buoyant means floating upon said reactants supporting the pond in spaced relation thereabove to leave a gas-filled space therebetween.

5. The anaerobic digestion system as set forth in claim 1 in which: the reactants are of a type that decompose upon anaerobic digestion within the reaction vessel to produce bio-gas and a pumpable effluent as reaction products; and, in which said pumpable effluent comprises the liquid heat exchange medium covering the lid.

6. The reaction vessel of claim 1 wherein the pond is floated upon the reactants so as to leave a dead air space therebetween that minimizes the direct exchange of heat from one to the other.

7. The method of anaerobically digesting decomposable organic material which comprises: introducing bio-degradable organic reactants into an open-topped reaction vessel, covering said reaction vessel with a fluid-filled pond exposed to the sun so as to produce a sealed chamber therein, insulating said pond from the reactants so as to minimize the direct exchange of heat from the sun-warmed liquid to said reactants, fermenting the reactants within said sealed chamber so as to generate a gas therefrom, removing the sun-warmed liquid from the pond and adjusting the temperature thereof, passing the liquid with its temperature thus adjusted in heat-exchange relation to the fermenting reactants in a manner to maintain same at a near constant pre-selected temperature effective to promote anaerobic digestion, and removing the gas thus generated.

8. The method as set forth in claim 7 which includes the additional steps of: introducing the reactants into the reaction vessel in the form of a pumpable slurry, and using the effluent from the fermentation reaction as the liquid heat transfer medium with which the pond is filled.

9. The method as set forth in claim 7 which includes the step of: floating the liquid-filled pond upon the reactants in the reaction vessel so as to maintain a gas-filled space therebetween.

10. The method as set forth in claim 7 which includes the step of: inflating an air-supported translucent dome over the pond as a protective cover therefor.

11. The method as set forth in claim 10 which includes the steps of: trapping the fluid evaporated from the pond during the daylight hours beneath the translucent dome covering same, and condensing the fluid thus evaporated on the relatively colder dome surface during the nighttime so as to create an artificial environment inside the latter effective to protect the reactants against extreme changes in ambient temperature.

* * * * *